United States Patent
Rölle et al.

(10) Patent No.: US 8,808,946 B2
(45) Date of Patent: *Aug. 19, 2014

(54) URETHANE ACRYLATE HAVING A HIGH REFRACTIVE INDEX AND REDUCED DOUBLE BOND DENSITY

(75) Inventors: Thomas Rölle, Leverkusen (DE); Friedrich-Karl Bruder, Krefeld (DE); Thomas Fäcke, Leverkusen (DE); Marc-Stephan Weiser, Leverkusen (DE); Dennis Hönel, Zülpich (DE)

(73) Assignee: Bayer MaterialScience AG, Monheim (DE)

( * ) Notice: Subject to any disclaimer, the term of this patent is extended or adjusted under 35 U.S.C. 154(b) by 92 days.

This patent is subject to a terminal disclaimer.

(21) Appl. No.: 13/504,190

(22) PCT Filed: Nov. 2, 2010

(86) PCT No.: PCT/EP2010/066588
§ 371 (c)(1),
(2), (4) Date: Apr. 26, 2012

(87) PCT Pub. No.: WO2011/054792
PCT Pub. Date: May 12, 2011

(65) Prior Publication Data
US 2012/0214895 A1 Aug. 23, 2012

(30) Foreign Application Priority Data
Nov. 3, 2009 (EP) .................................... 09013772

(51) Int. Cl.
*G03H 1/02* (2006.01)
*C07F 9/12* (2006.01)
*C07F 9/18* (2006.01)
*C08G 18/28* (2006.01)
*C08G 18/42* (2006.01)
*C08G 18/67* (2006.01)
*C08G 18/77* (2006.01)
*C08G 18/71* (2006.01)
*C08G 18/78* (2006.01)

(52) U.S. Cl.
CPC .......... *G03H 1/02* (2013.01); *G03H 2001/0264* (2013.01); *G03H 2260/12* (2013.01); *C07F 9/12* (2013.01); *C07F 9/18* (2013.01); *C08G 18/2885* (2013.01); *C08G 18/4277* (2013.01); *C08G 18/672* (2013.01); *C08G 18/776* (2013.01); *C08G 18/71* (2013.01); *C08G 18/7887* (2013.01)
USPC ........................................ 430/1; 430/2; 359/3

(58) Field of Classification Search
None
See application file for complete search history.

(56) References Cited

U.S. PATENT DOCUMENTS 5,747,629 A * 5/1998 Yeske et al. .................... 528/70
6,403,702 B1 * 6/2002 Markusch et al. ............. 524/590

(Continued)

FOREIGN PATENT DOCUMENTS

EP          0223587  A1   5/1987
WO   WO-2005093516  A1   10/2005

(Continued)

OTHER PUBLICATIONS

Wypych, Handbook of Plasticizers, Chapter 2, pp. 7-71 (2004).*

(Continued)

*Primary Examiner* — Martin Angebranndt
(74) *Attorney, Agent, or Firm* — Drinker Biddle & Reath LLP

(57) ABSTRACT

The invention relates to novel specially substituted urethane acrylates based on tris(p-isocyanatophenyl)thiophosphate having a high refractive index and reduced double bond density, and to a method for the production and use thereof.

17 Claims, 3 Drawing Sheets

(56) References Cited

U.S. PATENT DOCUMENTS

| | | |
|---|---|---|
| 7,981,987 B2 * | 7/2011 | Stockel et al. ............... 526/301 |
| 2003/0087104 A1 * | 5/2003 | Dhar et al. ................ 428/422.8 |
| 2003/0087163 A1 * | 5/2003 | Otaki et al. ...................... 430/1 |
| 2005/0058911 A1 * | 3/2005 | Takeyama ....................... 430/1 |
| 2008/0268374 A1 * | 10/2008 | Tashiro et al. ............ 430/280.1 |
| 2010/0086860 A1 * | 4/2010 | Roelle et al. .................... 430/2 |
| 2010/0087564 A1 * | 4/2010 | Weiser et al. ................... 522/95 |
| 2011/0207029 A1 * | 8/2011 | Hagen et al. .................... 430/2 |
| 2011/0236803 A1 * | 9/2011 | Weiser et al. ................... 430/2 |
| 2011/0311906 A1 * | 12/2011 | Rolle et al. ..................... 430/2 |
| 2012/0214089 A1 * | 8/2012 | Honel et al. .................... 430/2 |
| 2012/0214090 A1 * | 8/2012 | Weiser et al. ................... 430/2 |
| 2012/0219883 A1 * | 8/2012 | Bruder et al. .................... 430/2 |
| 2012/0219884 A1 * | 8/2012 | Weiser et al. ................... 430/2 |
| 2012/0231376 A1 * | 9/2012 | Rolle et al. ..................... 430/2 |
| 2012/0231377 A1 * | 9/2012 | Weiser et al. ................... 430/2 |
| 2012/0237856 A1 * | 9/2012 | Rolle et al. ..................... 430/2 |
| 2012/0321998 A1 * | 12/2012 | Rolle et al. ..................... 430/2 |
| 2013/0224634 A1 * | 8/2013 | Berneth et al. .................. 430/2 |

FOREIGN PATENT DOCUMENTS

| | | |
|---|---|---|
| WO | WO-2005114331 A1 | 12/2005 |
| WO | WO-2008/125199 A1 | 10/2008 |
| WO | WO-2008/125229 A1 | 10/2008 |

OTHER PUBLICATIONS

International Search Report for PCT/EP2010/066588 mailed Feb. 4, 2011.

* cited by examiner

URETHANE ACRYLATE HAVING A HIGH REFRACTIVE INDEX AND REDUCED DOUBLE BOND DENSITY

CROSS-REFERENCE TO RELATED APPLICATIONS

This application is a national stage application (under 35 U.S.C. §371) of PCT/EP2010/066588, filed Nov. 2, 2010, which claims benefit of European application 09013772.0, filed Nov. 3, 2009, both of which are incorporated herein by reference in their entirety for all their useful purposes.

BACKGROUND

The invention relates to novel specially substituted urethane acrylates based on tris(p-isocyanatophenyl)thiophosphate having a high refractive index and reduced double bond density and to a process for the preparation thereof. In addition, the invention relates to a photopolymer formulation comprising the urethane acrylates and the use of the photopolymer formulation.

For the uses of photopolymer formulations in the fields of use described below, the refractive index modulation $\Delta n$ produced by the holographic exposure in the photopolymer plays a decisive role. In the holographic exposure, the interference field comprising signal and reference light beam (in the simplest case, the two plane waves) is formed by the local photopolymerization of, for example, highly refracting acrylates at sites of high intensity in the interference field in a refractive index grating. The refractive index grating in the photopolymer (the hologram) contains all information of the signal light beam. By illuminating the hologram only with the reference light beam, the signal can then be reconstructed again. The strength of the signal thus reconstructed in relation to the strength of the incident reference light is referred to as Diffraction Efficiency, or DE below.

In the simplest case of a hologram which forms from the superposition of two plane waves, the DE is obtained from the quotient of the intensity of the light diffracted in the reconstruction and the sum of the intensities of incident reference light and diffracted light. The higher the DE, the more efficient is a hologram with respect to the necessary quantity of reference light, which is necessary for making the signal visible with a fixed brightness.

Highly refracting acrylates are capable of producing refractive index gratings with high amplitude between regions with lowest refractive index and regions with highest refractive index and hence permitting holograms having high DE and high $\Delta n$ in photopolymer formulations. It should be noted that the DE depends on the product of $\Delta n$ and the photopolymer layer thickness d. The greater the product, the greater is the possible DE (for reflection holograms).

The width of the angular range in which the hologram is visible (reconstructed), for example in the case of monochromatic illumination, depends only on the layer thickness d. On illumination of the hologram with, for example, white light, the width of the spectral range which can contribute to the reconstruction of the hologram likewise depends only on the layer thickness d. It is true that the smaller d, the greater the respective acceptance widths.

If it is intended to produce light and easily visible holograms, a high $\Delta n$ and a low thickness d are desirable, in particular so that DE is as large as possible. This means that the higher $\Delta n$, the more latitude there is for producing light holograms by adaptation of d and without loss of DE. The optimization of $\Delta n$ in the optimization of photopolymer formulations is therefore of outstanding importance.

WO 2008/125229 A1 describes photopolymer formulations which are suitable for producing holograms. These comprise polyurethane-based matrix polymers, acrylate-based writing monomers and photoinitiators. In the cured state, the writing monomers and the photoinitiators are embedded with spatial distribution in the polyurethane matrix. The WO document likewise discloses the addition of dibutyl phthalate, a classical plasticizer for industrial plastics, to the photopolymer formulation.

The holograms obtainable with the aid of the known photopolymer formulation have an insufficient trueness of colour or trueness of angle, i.e. the colours or angles at which the holograms were recorded are not reproduced in the desired manner in the reconstruction of the holograms, i.e. only insufficiently close to the recording conditions of the hologram.

In the following section "Measurement of the holographic properties DE and $\Delta n$ of the holographic media by means of two-beam interference in reflection arrangement", it is shown that, owing to resulting shrinkage and owing to changes in the mean refractive index in the photopolymerization of the writing monomers, the angle difference between recording and reconstruction angles must be corrected. The change in the refractive index results mainly from the change of the density of the material on transformation from the monomer to the polymer. In visual holograms, shrinkage leads to insufficient trueness of colour, i.e. the original wavelength which was used for the holographic recording of the object is shifted to shorter wavelength in the reconstruction with the same geometry. In holographic optical elements, in the simplest case of a grating, shrinkage also leads to insufficient trueness of angle.

Particularly if the identical wavelength is used for the holographic recording of simple reflection gratings, the peak shift $(\alpha_0'-\alpha_0)$ between the reconstruction angle with maximum diffraction efficiency $\alpha_0'$ and the recording angle $\alpha_0$ should be taken into account. In order nevertheless to obtain high trueness of colour and high trueness of angle between recorded and reproduced hologram, a certain effort must therefore be made for angle or wavelength correction or other optical measures must be carried out for compensation.

BRIEF DESCRIPTION OF EMBODIMENTS

It was therefore an object of the present invention to provide an acrylate-based writing monomer for a photopolymer formulation, with the aid of which it is possible to produce holograms which have improved trueness of colour and trueness of angle and in particular have a reduced peak shift with comparable brightness.

This object is achieved by a urethane acrylate of the formula (I)

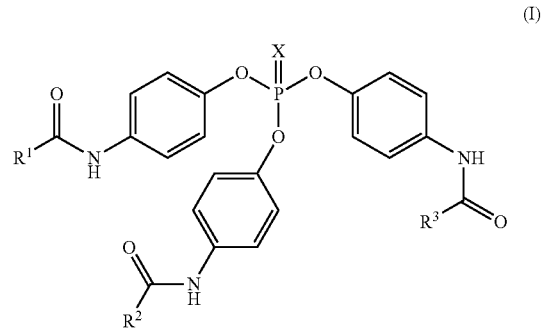

(I)

in which X is oxygen or sulphur, and $R^1$, $R^2$, $R^3$, independently of one another, are each an olefinically unsaturated organic radical or an aliphatic alcohol, at least one of the radicals $R^1$, $R^2$, $R^3$ being an olefinically unsaturated organic radical and at least one of the radicals $R^1$, $R^2$, $R^3$ being an aliphatic alcohol.

Thus, it was found that photopolymer formulation holograms having high trueness of colour and high trueness of angle can be produced if the urethane acrylate according to the invention is used as a writing monomer in a photopolymer formulation. The trueness of colour and trueness of angle of these holograms are higher than those of the holograms which are obtainable with the aid of the photopolymer formulations of WO 2008/125229 A1.

BRIEF DESCRIPTION OF THE DRAWINGS

The foregoing brief description, as well as the following detailed description, may be better understood when read in conjunction with the appended drawings. For the purpose of assisting in the explanation of the invention, there are shown in the drawings representative embodiments which are considered illustrative. It should be understood, however, that the invention is not limited in any manner to the precise arrangements and instrumentalities shown. In the drawings.

DETAILED DESCRIPTION OF EMBODIMENTS

Figure 1:
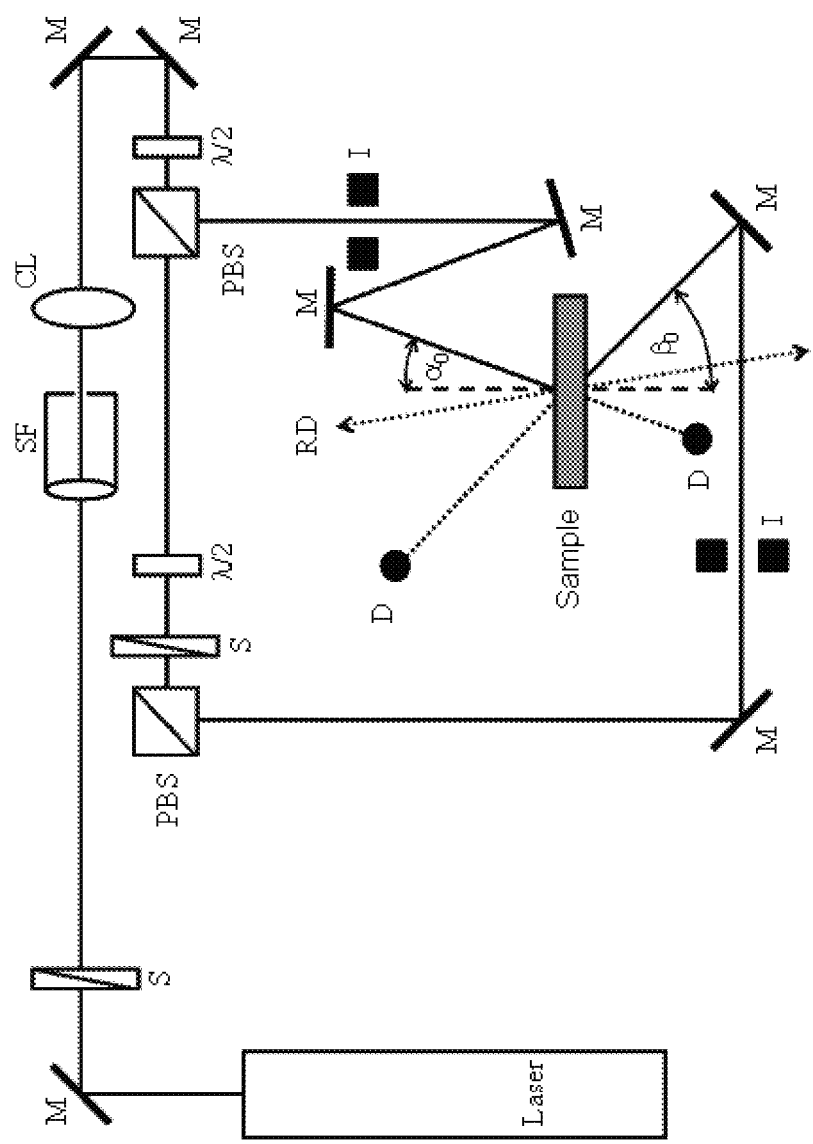
FIG. 1 illustrates a measuring arrangement.

According to a preferred embodiment, it is envisaged that the aliphatic alcohol or alcohols is or are substituted by at least one fluorine atom. In this case, it is possible to obtain holograms which have a substantially reduced peak shift, i.e. require substantially fewer compensatory measures in the recording and the reconstruction of the holograms with regard to trueness of colour and trueness of angle.

It is also preferable if the aliphatic alcohol or alcohols has or have linear or branched C1-C10 radicals, preferably linear $C_2$-$C_4$ or branched $C_3$-alkyl radicals.

Particularly good results can be achieved if the aliphatic alcohols are trifluoroethanol and/or 1,1,1,3,3,3-hexafluoropropan-2-ol.

In a further development of the invention, it is intended that the olefinically unsaturated organic radical or radicals has or have acrylate or methacrylate structures.

Furthermore, it is preferable if the olefinically unsaturated organic radical or radicals is or are substituted by one or more heteroatoms.

The invention furthermore relates to a photopolymer formulation comprising matrix polymers, writing monomers and photoinitiators, in which the writing monomers comprise a urethane acrylate according to any of claims 1 to 6.

The matrix polymers may be in particular polyurethanes.

Preferably, the polyurethanes are obtainable by reacting an isocyanate component a) with an isocyanate-reactive component b).

The isocyanate component a) preferably comprises polyisocyanates. Polyisocyanates which may be used are all compounds well known per se to the person skilled in the art or mixtures thereof, which have on average two or more NCO functions per molecule. These may have an aromatic, araliphatic, aliphatic or cycloaliphatic basis. In minor amounts, monoisocyanates and/or polyisocyanates containing unsaturated groups may also be concomitantly used.

For example, butylene diisocyanate, hexamethylene diisocyanate (HDI), isophorone diisocyanate (IPDI), 1,8-diisocyanato-4-(isocyanatomethyl)octane, 2,2,4- and/or 2,4,4-trimethylhexamethylene diisocyanate, the isomeric bis(4,4'-isocyanatocyclohexyl)methanes and mixtures thereof having any desired isomer content, isocyanatomethyl-1,8-octane diisocyanate, 1,4-cyclohexylene diisocyanate, the isomeric cyclohexanedimethylene diisocyanates, 1,4-phenylene diisocyanate, 2,4- and/or 2,6-toluylene diisocyanate, 1,5-naphthylene diisocyanate, 2,4'- or 4,4'-diphenylmethane diisocyanate and/or triphenylmethane 4,4',4"-triisocyanate are suitable.

The use of derivatives of monomeric di- or triisocyanates having urethane, urea, carbodiimide, acylurea, isocyanurate, allophanate, biuret, oxadiazinetrione, uretdione and/or iminooxadiazinedione structures is also possible.

The use of polyisocyanates based on aliphatic and/or cycloaliphatic di- or triisocyanates is preferred.

Particularly preferably, the polyisocyanates of component a) are dimerized or oligomerized aliphatic and/or cycloaliphatic di- or triisocyanates.

Isocyanurates, uretdiones and/or iminooxadiazinediones based on HDI, 1,8-diisocyanato-4-(isocyanatomethyl)octane or mixtures thereof are very particularly preferred.

NCO-functional prepolymers having urethane, allophanate, biuret and/or amide groups can likewise be used as component a). Prepolymers of component a) are obtained in a manner well known per se to the person skilled in the art by reacting monomeric, oligomeric or polyisocyanates a1) with isocyanate-reactive compounds a2) in suitable stoichiometry with optional use of catalysts and solvents.

Suitable polyisocyanates a1) are all aliphatic, cycloaliphatic, aromatic or araliphatic di- and triisocyanates known per se to the person skilled in the art, it being unimportant whether these were obtained by means of phosgenation or by phosgene-free processes. In addition, the higher molecular weight secondary products of monomeric di- and/or triisocyanates having a urethane, urea, carbodiimide, acylurea, isocyanurate, allophanate, biuret, oxadiazinetrione, uretdione or iminooxadiazinedione structure, which are well known per se to the person skilled in the art, can also be used in each case individually or in any desired mixtures with one another.

Examples of suitable monomeric di- or triisocyanates which can be used as component a1) are butylene diisocyanate, hexamethylene diisocyanate (HDI), isophorone diisocyanate (IPDI), trimethylhexamethylene diisocyanate (TMDI), 1,8-diisocyanato-4-(isocyanatomethyl)octane, isocyanatomethyl-1,8-octane diisocyanate (TIN), 2,4- and/or 2,6-toluene diisocyanate.

OH-functional compounds are preferably used as isocyanate-reactive compounds a2) for the synthesis of the prepolymers. These are analogous to the OH-functional compounds as described below for the component b).

The use of amines for the prepolymer preparation is also possible. For example, ethylenediamine, diethylenetriamine, triethylenetetramine, propylenediamine, diaminocyclohexane, diaminobenzene, diaminobisphenyl, difunctional polyamines, such as, for example, the Jeffamines®, amineterminated polymers having number average molar masses of up to 10 000 g/mol, or any desired mixtures thereof with one another are suitable.

For the preparation of prepolymers containing biuret groups, isocyanate is reacted in excess with amine, a biuret group forming. In this case, suitable amines for the reaction with the di-, tri- and polyisocyanates mentioned are all oligomeric or polymeric, primary or secondary, difunctional amines of the abovementioned type.

Preferred prepolymers are urethanes, allophanates or biurets obtained from aliphatic isocyanate-functional compounds and oligomeric or polymeric isocyanate-reactive compounds having number average molar masses of 200 to 10 000 g/mol; urethanes, allophanates or biurets obtained from aliphatic isocyanate-functional compounds and oligomeric or polymeric polyols or polyamines having number average molar masses of 500 to 8500 g/mol are particularly preferred and allophanates obtained from HDI or TMDI and difunctional polyetherpolyols having number average molar masses of 1000 to 8200 g/mol are very particularly preferred.

The prepolymers described above preferably have residual contents of free monomeric isocyanates of less than 1% by weight, particularly preferably less than 0.5% by weight, very particularly preferably less than 0.2% by weight.

Of course, the isocyanate component may contain proportionately further isocyanate components in addition to the prepolymers described. Aromatic, araliphatic, aliphatic and cycloaliphatic di-, tri- or polyisocyanates are suitable for this purpose used. It is also possible to use mixtures of such di-, tri- or polyisocyanates. Examples of suitable di-, tri- or polyisocyanates are butylene diisocyanate, hexamethylene diisocyanate (HDI), isophorone diisocyanate (IPDI), 1,8-diisocyanato-4-(isocyanatomethyl)octane, 2,2,4- and/or 2,4,4-trimethylhexamethylene diisocyanate (TMDI), the isomeric bis(4,4'-isocyanatocyclohexyl)methanes and mixtures thereof having any desired isomer content, isocyanatomethyl-1,8-octane diisocyanate, 1,4-cyclohexylene diisocyanate, the isomeric cyclohexanedimethylene diisocyanates, 1,4-phenylene diisocyanate, 2,4- and/or 2,6-toluylene diisocyanate, 1,5-naphthylene diisocyanate, 2,4'- or 4,4'-diphenylmethane diisocyanate, triphenyl-methane 4,4',4"-triisocyanate or derivatives thereof having a urethane, urea, carbodiimide, acylurea, isocyanurate, allophanate, biuret, oxadiazinetrione, uretdione or iminooxadiazinedione structure and mixtures thereof. Polyisocyanates based on oligomerized and/or derivatized diisocyanates which were freed from excess diisocyanate by suitable processes are preferred, in particular those of hexamethylene diisocyanate. The oligomeric isocyanurates, uretdiones and iminooxadiazinediones of HDI and mixtures thereof are particularly preferred.

It is optionally also possible for the isocyanate component a) proportionately to contain isocyanates which are partly reacted with isocyanate-reactive ethylenically unsaturated compounds. α,β-unsaturated carboxylic acid derivatives, such as acrylates, methacrylates, maleates, fumarates, maleimides, acrylamides, and vinyl ethers, propenyl ethers, allyl ethers and compounds which contain dicyclopentadienyl units and have at least one group reactive towards isocyanates are preferably used here as isocyanate-reactive ethylenically unsaturated compounds; these are particularly preferably acrylates and methacrylates having at least one isocyanate-reactive group. Suitable hydroxy-functional acrylates or methacrylates are, for example, compounds such as 2-hydroxyethyl (meth)acrylate, polyethylene oxide mono(meth)acrylates, polypropylene oxide mono(meth)acrylates, polyalkylene oxide mono(meth)acrylates, poly(E-caprolactone) mono(meth)-acrylates, such as, for example, Tone® M100 (Dow, USA), 2-hydroxypropyl (meth)acrylate, 4-hydroxybutyl (meth)acrylate, 3-hydroxy-2,2-dimethylpropyl (meth)acrylate, the hydroxy-functional mono-, di- or tetra(meth)acrylates of polyhydric alcohols, such as trimethylolpropane, glycerol, pentaerythritol, dipentaerythritol, ethoxylated, propoxylated or alkoxylated trimethylolpropane, glycerol, pentaerythritol, dipentaerythritol or the industrial mixtures thereof. In addition, isocyanate-reactive oligomeric or polymeric unsaturated compounds containing acrylate and/or methacrylate groups, alone or in combination with the abovementioned monomeric compounds, are suitable. The proportion of isocyanates which are partly reacted with isocyanate-reactive ethylenically unsaturated compounds, based on the isocyanate component a), is 0 to 99%, preferably 0 to 50%, particularly preferably 0 to 25% and very particularly preferable 0 to 15%.

It is optionally also possible for the abovementioned isocyanate component a) completely or proportionately to contain isocyanates which are reacted completely or partly with blocking agents known to the person skilled in the art from coating technology. The following may be mentioned as an example of blocking agents: alcohols, lactams, oximes, malonic esters, alkyl acetoacetates, triazoles, phenols, imidazoles, pyrazoles and amines, such as, for example, butanone oxime, diisopropylamine, 1,2,4-triazole, dimethyl-1,2,4-triazole, imidazole, diethyl malonate, ethyl acetoacetate, acetone oxime, 3,5-dimethylpyrazole, E-caprolactam, N-tert-butylbenzylamine, cyclopentanone carboxyethyl ester or any desired mixtures of these blocking agents.

In principle, all polyfunctional, isocyanate-reactive compounds which have on average at least 1.5 isocyanate-reactive groups per molecule can be used as component b).

Isocyanate-reactive groups in the context of the present invention are preferably hydroxyl, amino or thio groups, and hydroxy compounds are particularly preferred.

Suitable polyfunctional, isocyanate-reactive compounds are, for example, polyesterpolyols, polyetherpolyols, polycarbonatepolyols, poly(meth)acrylatepolyols and/or polyurethanepolyols.

Suitable polyesterpolyols are, for example, linear polyesterdiols or branched polyesterpolyols as obtained in a known manner from aliphatic, cycloaliphatic or aromatic di- or polycarboxylic acids or their anhydrides with polyhydric alcohols having an OH functionality of >2.

Examples of such di- or polycarboxylic acids or anhydrides are succinic, glutaric, adipic, pimelic, suberic, azelaic, sebacic, nonanedicarboxylic, decanedicarboxylic, terephthalic, isophthalic, o-phthalic, tetrahydrophthalic, hexahydrophthalic or trimellitic acid and acid anhydrides, such as o-phthalic, trimellitic or succinic anhydride, or any desired mixtures thereof with one another.

Examples of such suitable alcohols are ethanediol, di-, triand tetraethylene glycol, 1,2-propanediol, di-, tri- and tetrapropylene glycol, 1,3-propanediol, 1,4-butanediol, 1,3-butanediol, 2,3-butanediol, 1,5-pentanediol, 1,6-hexanediol, 2,2-dimethyl-1,3-propanediol, 1,4-di-hydroxycyclohexane, 1,4-dimethylolcyclohexane, 1,8-octanediol, 1,10-decanediol, 1,12-dodecanediol, trimethylolpropane, glycerol or any desired mixtures thereof with one another.

The polyesterpolyols may also be based on natural raw materials, such as castor oil. It is also possible for the polyesterpolyols to be based on homo- or copolymers of lactones, as can preferably be obtained by addition reaction of lactones or lactone mixtures, such as butyrolactone, ε-caprolactone and/or methyl-ε-caprolactone, with hydroxy-functional compounds, such as polyhydric alcohols having an OH functionality of ≥2, for example of the abovementioned type.

Such polyesterpolyols preferably have number average molar masses of 400 to 4000 g/mol, particularly preferably of 500 to 2000 g/mol. Their OH functionality is preferably 1.5 to 3.5, particularly preferably 1.8 to 3.0.

Suitable polycarbonatepolyols are obtainable in a manner known per se by reacting organic carbonates or phosgene with diols or diol mixtures.

Suitable organic carbonates are dimethyl, diethyl and diphenyl carbonate.

Suitable diols or mixtures comprise the polyhydric alcohols mentioned in relation to the polyester segments and having an OH functionality of ≥2, preferably 1,4-butanediol, 1,6-hexanediol and/or 3-methylpentanediol, or polyesterpolyols can be converted into polycarbonatepolyols.

Such polycarbonatepolyols preferably have number average molar masses of 400 to 4000 g/mol, particularly preferably of 500 to 2000 g/mol. The OH functionality of these polyols is preferably 1.8 to 3.2, particularly preferably 1.9 to 3.0.

Suitable polyetherpolyols are optionally polyadducts of cyclic ethers with OH- or NH-functional starter molecules, which polyadducts have a block structure.

Suitable cyclic ethers are, for example, styrene oxides, ethylene oxide, propylene oxide, tetrahydrofuran, butylene oxide, epichlorohydrin and any desired mixtures thereof.

The polyhydric alcohols mentioned per se in the context of the polyesterpolyols and having an OH functionality of ≥2 and primary or secondary amines and aminoalcohols can be used as starters.

Preferred polyetherpolyols are those of the abovementioned type, exclusively based on propylene oxide or random or block copolymers based on propylene oxide with further 1-alkylene oxides, the proportion of 1-alkylene oxides not being higher than 80% by weight. In addition, poly(trimethylene oxides) according to formula (III) and mixtures of the polyols mentioned as being preferred are preferred. Propylene oxide homopolymers and random or block copolymers which have oxyethylene, oxypropylene and/or oxybutylene units are particularly preferred, the proportion of the oxypropylene units, based on the total amount of all oxyethylene, oxypropylene and oxybutylene units, accounting for at least 20% by weight, preferably at least 45% by weight. Here, oxypropylene- and oxybutylene- comprise all respective linear and branched C3- and C4-isomers.

Such polyetherpolyols preferably have number average molar masses of 250 to 10 000 g/mol, particularly preferably of 500 to 8500 g/mol and very particularly preferably of 600 to 4500 g/mol. The OH functionality is preferably 1.5 to 4.0, particularly preferably 1.8 to 3.1.

In addition, short-chain, aliphatic, araliphatic or cycloaliphatic di-, tri- or polyfunctional alcohols which have a low molecular weight, i.e. having molecular weights of less than 500 g/mol, i.e. contain 2 to 20 carbon atoms, are also suitable as constituents of component b) as polyfunctional, isocyanate-reactive compounds.

These may be, for example, ethylene glycol, diethylene glycol, triethylene glycol, tetraethylene glycol, dipropylene glycol, tripropylene glycol, 1,2-propanediol, 1,3-propanediol, 1,4-butanediol, neopentyl glycol, 2-ethyl-2-butyl-propanediol, trimethylpentanediol, positional isomers of diethyloctanediol, 1,3-butylene glycol, cyclohexanediol, 1,4-cyclohexanedimethanol, 1,6-hexanediol, 1,2- and 1,4-cyclohexanediol, hydrogenated bisphenol A (2,2-bis(4-hydroxycyclo-hexyl)propane), 2,2-dimethyl-3-hydroxypropyl 2,2-dimethyl-3-hydroxypropionate. Examples of suitable triols are trimethylolethane, trimethylolpropane or glycerol. Suitable higher-functional alcohols are ditrimethylolpropane, pentaerythritol, dipentaerythritol or sorbitol.

The photoinitiators used are usually initiators which can be activated by actinic radiation and which initiate polymerization of the corresponding polymerizable groups. Photoinitiators are commercially distributed compounds known per se, a distinction being made between monomolecular (type I) and bimolecular (type II) initiators. Furthemore, depending on their chemical nature, these intiators are used for free radical, anionic (or) cationic (or mixed) forms of the abovementioned polymerizations.

The photoinitiators may comprise in particular an anionic, cationic or neutral dye and a coinitiator.

(Type I) systems for free radical photopolymerization are, for example, aromatic ketone compounds, e.g. benzophenones in combination with tertiary amines, alkylbenzophenones, 4,4'-bis(dimethylamino)benzophenone (Michlers ketone), anthrone and halogenated benzophenones or mixtures of said types. Also suitable are (type II) initiators, such as benzoin and its derivatives, benzil ketals, acylphosphine oxides, e.g. 2,4,6-trimethylbenzoyldiphenylphosphine oxide, bisacylophosphine oxides, phenylglyoxylic acid esters, camphorquinone, alpha-aminoalkylphenones, alpha-,alpha-dialkoxyacetophenones, 1-[4-(phenylthio)phenyl]octane-1,2-dione 2-(O-benzoyloxime) and alpha-hydroxyalkylphenones. The photoinitiator systems described in EP-A 0223587 and consisting of a mixture of one ammonium arylborate and one or more dyes can also be used as a photoinitiator. For example, tetrabutylammonium triphenylhexylborate, tetrabutylammonium triphenylbutylborate, tetrabutylammonium trinapthylhexylborate, tetrabutylammonium tris(4-tert-butyl)phenylbutylborate, tetrabutylammonium tris(3-fluorophenyl)hexylborate, tetramethylammonium triphenylbenzylborate, tetra(n-hexyl) ammonium (sec-butyl)triphenylborate, 1-methyl-3-octylimidazolium dipentyldiphenylborate and tetrabutylammonium tris(3-chloro-4-methylphenyl)hexylborate are suitable as the ammonium arylborate. Suitable dyes are, for example, new methylene blue, thionine, Basic Yellow, pinacynol chloride, rhodamine 6G, gallocyanine, ethyl violet, Victoria Blue R, Celestine Blue, quinaldine red, crystal violet, brilliant green, astrazone orange G, Darrow Red, pyronine Y, Basic Red 29, pyrillium I, cyanine and methylene blue, azure A (Cunningham et al., RadTech'98 North America UV/EB Conference Proceedings, Chicago, Apr. 19-22, 1998).

The photoinitiators used for the anionic polymerization are as a rule (type I) systems and are derived from transition metal complexes of the first series. Here are chromium salts, such as, for example, trans-$Cr(NH_3)_2(NCS)_4$— (Kutal et al., Macromolecules 1991, 24, 6872) or ferrocenyl compounds (Yamaguchi et al., Macromolecules 2000, 33, 1152). Another possibility of anionic polymerization consists in the use of dyes, such as crystal violet leuconitrile or malchite green leuconitrile, which can polymerize cyanoacrylates by photolytic decomposition (Neckers et al., Macromolecules 2000, 33, 7761). However, the chromophore is incorporated into the polymer here, such that the resulting polymers are colored throughout.

The photoinitiators used for the cationic polymerization substantially consist of three classes: aryldiazonium salts, onium salts (here especially: iodonium, sulfonium and selenonium salts) and organometallic compounds. On irradiation, both in the presence and in the absence of a hydrogen donor, phenyldiazonium salts can produced a cation that initiates the polymerization. The efficiency of the total system is determined by the nature of the counterion used for the diazonium compound. The not very reactive but very expensive $SbF_6^-$, AsF$_6^-$ or PF$_6^-$ is preferred here. These compounds as a rule are not very suitable for use in the coating of thin films, since the the nitrogen released after the exposure the surface quality is reduced (pinholes) (Li et al., Polymeric Materials Science and Engineering, 2001, 84, 139). Onium salts, especially sulfonium and iodonium salts, are very widely used and also commercially available in many forms. The photochemistry of these compounds has been investigated for a long time. After excitation, the iodonium salts initially decompose homolytically and thus produce a free radical and a radical anion which is stabilized by H abstraction and liberates a proton and then initiates the cationic polymerization (Dektar et al., J. Org. Chem. 1990, 55, 639; J. Org. Chem., 1991, 56, 1838). This mechanism permits the use of iodonium salts also for free radical polymerization. Once again, the choice of the counterion is of considerable importance here, the very expensive SbF$_6^-$, AsF$_6^-$ or PF$_6^-$ is likewise preferred. Otherwise, the choice of substitution of the aromatic is entirely free in this structure class and is substantially determined by the availability of suitable starting building blocks for the synthesis. The sulfonium salts are compounds which decompose in according to Norrish(II) (Crivello et al., Macromolecules, 2000, 33, 825). In the case of the sulfonium salts, too, the choice of the counterion is of critical importance, which manifests itself substantially in the curing rate of the polymers. The best results are obtained as a rule with SbF$_6^-$ salts. Since the self-absorption of iodonium and sulfonium salts occurs at <300 nm, these compounds must be appropriately sensitized for the photopolymerization with near UV or shortwave visible light. This is effected by the use of relatively highly absorbing aromatics, such as, for exmaple, anthracene and derivatives (Gu et al., Am. Chem. Soc. Polymer Preprints, 2000, 41 (2), 1266) or phenothiazine or derivatives thereof (Hua et al, Macromolecules 2001, 34, 2488-2494).

It may also be advantageous to use mixtures of these compounds. Depending on the radiation source used for the curing, type and concentration of photoinitiator must be adapted in a manner known to the person skilled in the art. Further details are described, for example, in P. K. T. Oldring (ed.), Chemistry & Technology of UV & EB Formulations For Coatings, Inks & Paints, Vol. 3, 1991, SITA Technology, London, pages 61-328.

Preferred photoinitiators are mixtures of tetrabutylammonium tetrahexylborate, tetrabutylammonium triphenylhexylborate, tetrabutylammonium tris(3-fluorophenyl)hexylborate and tetrabutylammonium tris(3-chloro-4-methylphenyl) hexylborate with dyes, such as, for example, astrazone orange G, methylene blue, new methylene blue, azure A, pyrillium I, safranine O, cyanine, gallocyanine, brilliant green, crystal violet, ethyl violet and thionine.

The photopolymer formulation may additionally contain urethanes as plasticizers, it being possible for the urethanes to be substituted in particular by at least one fluorine atom.

The urethanes can preferably have the general formula (III)

(III)

in which n≥1 and n≤8 and R$^4$, R$^5$, R$^6$ are hydrogen and/or, independently of one another, linear, branched, cyclic or heterocyclic organic radicals which are unsubstituted or optionally also substituted by heteroatoms, preferably at least one of the radicals R$^4$, R$^5$, R$^6$ being substituted by at least one fluorine atom and particularly preferably R$^4$ being an organic radical having at least one fluorine atom.

In a further preferred embodiment, it is envisaged that the writing monomers additionally comprise a monofunctional writing monomer, it being possible for this to be in particular a polyfunctional acrylate. The monofunctional acrylate can particularly preferably have the general formula (IV)

(IV)

in which R$^7$, R$^8$ are hydrogen and/or, independently of one another, linear, branched, cyclic or heterocyclic organic radicals which are unsubstituted or optionally also substituted by heteroatoms.

The invention furthermore relates to the use of a photopolymer formulation according to the invention for the production of holographic media, in particular for the production of in-line holograms, off-axis holograms, full-aperture transfer holograms, white light transmission holograms, Denisyuk holograms, off-axis reflection holograms, edge-lit holograms and holographic stereograms.

EXAMPLES

The invention is explained in more detail below with reference to examples.

Unless noted otherwise, all percentage data are based on percent by weight.

Methods of Measurement:

The refractive index n as a function of the wavelength of the samples were obtained from the transmission and reflection spectra. For this purpose, about 100-300 nm thick films of the samples were applied by spincoating to quartz glass substrates from dilute solution in butyl acetate. The transmission and reflection spectrum of this layer packet was measured with a spectrometer from STEAG ETA-Optik, CD-Measurement System ETA-RT, and the layer thickness and the spectral curve of n were then fitted to the measured transmission and reflection spectra. This is effected using the internal software of the spectrometer and additionally requires the n data of the quartz glass substrate, which were determined beforehand in a blank measurement.

The stated double bond density is calculated from the sum of the double bond densities of the olefinically unsaturated compounds used and the proportion thereof in % by weight in the formulation, with the unit eq/kg.

The stated NCO values (isocyanate contents) were determined according to DIN EN ISO 11909.

Measurement of the Holographic Properties DE and Δn of the Holographic Media by Means of Two-Beam Interference in Reflection Arrangement The media produced were then tested with regard to their holographic properties by means of a measuring arrangement according to FIG. 1, as follows:

The beam of an He—Ne laser (emission wavelength 633 nm) was converted with the aid of a spatial filter (SF) and together with the collimation lens (CL) into a parallel homogeneous beam. The final cross sections of the signal and reference beam are established by the iris diaphragms (I). The diameter of the iris diaphragm opening is 0.4 cm. The polarization-dependent beam splitters (PBS) split the laser beam into two coherent equally polarized beams. Via the λ/2 plates, the power of the reference beam was adjusted to 0.5 mW and the power of the signal beam to 0.65 mW. The powers were determined using the semiconductor detectors (D) with sample removed. The angle of incidence ($\alpha_0$) of the reference beam is −21.8° and the angle of incidence ($\beta_0$) of the signal beam is 41.8°. The angles are measured starting from the sample normals to the beam direction. According to FIG. 1, $\alpha_0$ therefore has a negative sign and $\beta_0$ a positive sign. At the location of the sample (medium), the interference field of the two overlapping beams produced a grating of light and dark strips which are perpendicular to the angle bisectors of the two beams incident on the sample (reflection hologram). The strip spacing Λ, also referred to as grating period, in the medium is ~225 nm (the refractive index of the medium assumed to be ~1.504).

FIG. 1 shows the geometry of a holographic media tester (HMT) at λ=633 nm (He—Ne laser): M=mirror, S=shutter, SF=spatial filter, CL=collimator lens, λ/2=λ/2 plate, PBS=polarization-sensitive beam splitter, D=detector, I=iris diaphragm, $\alpha_0$=−21.8°, $\beta_0$=41.8° are the angles of incidence of the coherent beams, measured outside the sample (outside the medium). RD=reference direction of the turntable.

The diffraction efficiency (DE) of the media were measured using an experimental holographic setup as shown in FIG. 1.

Holograms were recorded into the medium in the following manner:

Both shutters (S) are opened for the exposure time t.

Thereafter, with closed shutters (S), the medium is allowed a time of 5 minutes for the diffusion of the still unpolymerized writing monomers.

The holograms recorded were now read in the following manner. The shutter of the signal beam remained closed. The shutter of the reference beam was opened. The iris diaphragm of the reference beam was closed to a diameter of <1 mm. This ensured that the beam was always completely in the previously recorded hologram for all angles of rotation (Ω) of the medium. The turntable, under computer control, now covered the angle range from $\Omega_{min}$ to $\Omega_{max}$ with an angle step width of 0.05°. Ω is measured from the sample normal to the reference direction of the turnbtable. The reference direction of the turntable results when the angle of incidence of the reference beam and that of the signal beam are of the same magnitude, i.e. $\alpha_0$=−31.8° and $\beta_0$=31.8°, on recording of the hologram. $\Omega_{recording}$ is then 0°. For $\alpha_0$=−21.8° and $\beta_0$=41.8°, $\Omega_{recording}$ is therefore 10°. In general, the following is true of the interference field during recording of the hologram:

$$\alpha_0 = \theta_0 + \Omega_{recording}.$$

$\theta_0$ is the semiangle in the laboratory system outside the medium and the following is true during recording of the hologram:

$$\theta_0 = \frac{\alpha_0 - \beta_0}{2}.$$

In this case $\theta_0$ is therefore −31.8°. At each angle of rotation Ω approached, the powers of the beam transmitted in the zeroth order were measured by means of the corresponding detector D and the powers of the beam diffracted in the first order were measured by means of the detector D. The diffraction efficiency was obtained at each angle Ω approached as the quotient of:

$$\eta = \frac{P_D}{P_D + P_T}$$

$P_D$ is the power in the detector of the diffracted beam and $P_T$ is the power in the detector of the transmitted beam.

By means of the method described above, the Bragg curve (it describes the diffraction efficiency n as a function of the angle of rotation Ω of the recorded hologram) was measured and was stored in a computer. In addition, the intensity transmitted in the zeroth order was also plotted against the angle of rotation Ω and stored in a computer.

The maximum diffraction efficiency (DE=$\eta_{max}$) of the hologram, i.e. its peak value, was determined in the case of $\Omega_{reconstruction}$. It may have been necessary for this purpose to change the position of the detector of the diffracted beam in order to determine this maximum value.

The refractive index contrast Δn and the thickness d of the photopolymer layer were now determined by means of the coupled wave theory (cf.: H. Kogelnik, The Bell System Technical Journal, Volume 48, November 1969, Number 9 page 2909-page 2947) from the measured Bragg curve and the angle variation of the transmitted intensity. It is to be noted that, owing to the thickness shrinkage occurring as a result of the photopolymerization, the strip spacing Λ' of the hologram and the orientation of the strip (slant) may deviate from the strip spacing Λ of the interference pattern and the orientation thereof. Accordingly, the angle $\alpha_0$' or the corresponding angle of the turntable $\Omega_{reconstruction}$, at which maximum diffraction efficiency is achieved will also differ from $\alpha_0$ or from the corresponding $\Omega_{recording}$ respectively. As a result, the Bragg condition changes. This change is taken into account in the evaluation method. The evaluation method is described below:

All geometrical quantities which relate to the recorded hologram and not to the interference pattern are represented as quantities shown by dashed lines.

For the Bragg curve η (Ω) of a reflection hologram, the following is true according to Kogelnik:

$$\eta = \begin{cases} \dfrac{1}{1 - \dfrac{1-(\xi/\nu)^2}{\sin^2\left(\sqrt{\xi^2 - \nu^2}\right)}}, & \text{for } \nu^2 - \xi^2 < 0 \\ \dfrac{1}{1 + \dfrac{1-(\xi/\nu)^2}{\sinh^2\left(\sqrt{\nu^2 - \xi^2}\right)}}, & \text{for } \nu^2 - \xi^2 \geq 0 \end{cases}$$

with:

$$\nu = \frac{\pi \cdot \Delta n \cdot d'}{\lambda \cdot \sqrt{|c_s \cdot c_r|}}$$

$$\xi = -\frac{d'}{2 \cdot c_s} \cdot DP$$

$$c_s = \cos(\vartheta') - \cos(\psi') \cdot \frac{\lambda}{n \cdot \Lambda'}$$

$$c_r = \cos(\vartheta')$$

$$DP = \frac{\pi}{\Lambda'} \cdot \left(2 \cdot \cos(\psi' - \vartheta') - \frac{\lambda}{n \cdot \Lambda'}\right)$$

$$\psi' = \frac{\beta' + \alpha'}{2}$$

-continued $$\Lambda' = \frac{\lambda}{2 \cdot n \cdot \cos(\psi' - \alpha')}$$

On reading of the hologram ("reconstruction"), the following is true, as shown analogously above:

$\theta'_0 = \theta_0 + \Omega$ $\sin(\theta'_0) = n \cdot \sin(\theta')$

Under the Bragg condition, the "dephasing" DP is 0, and accordingly:

$\alpha'_0 = \theta_0 + \Omega_{reconstruction}$ $\sin(\alpha'_0) = n \cdot \sin(\alpha')$ The unknown angle $\beta'$ can be determined from comparison of the Bragg condition of the interference field during recording of the hologram and the Bragg condition during reading of the hologram, assuming that only thickness shrinkage takes place. Accordingly:

$$\sin(\beta') = \frac{1}{n} \cdot [\sin(\alpha_0) + \sin(\beta_0) - \sin(\theta_0 + \Omega_{reconstruction})]$$

$\upsilon$ is the grating thickness, $\xi$ is the detuning parameter and $\psi'$ is the orientation (slant) of the refractive index grating which was recorded, $\psi'$ and $\beta'$ corresponding to the angles $\alpha 0$ and $\beta 0$ of the interference field during recording of the hologram, but measured in the medium and applicable to the grating of the hologram (after thickness shrinkage). n is the mean refractive index of the photopolymer and was set at 1.504. $\lambda$ is the wavelength of the laser light in vacuo.

The maximum diffraction efficiency ($DE = \eta_{max}$) is then obtained for $\xi = 0$ as:

$$DE = \tanh^2(v) = \tanh^2\left(\frac{\pi \cdot \Delta n \cdot d'}{\lambda \cdot \sqrt{\cos(\alpha') \cdot \cos(\alpha' - 2\psi)}}\right)$$

Figure 2:
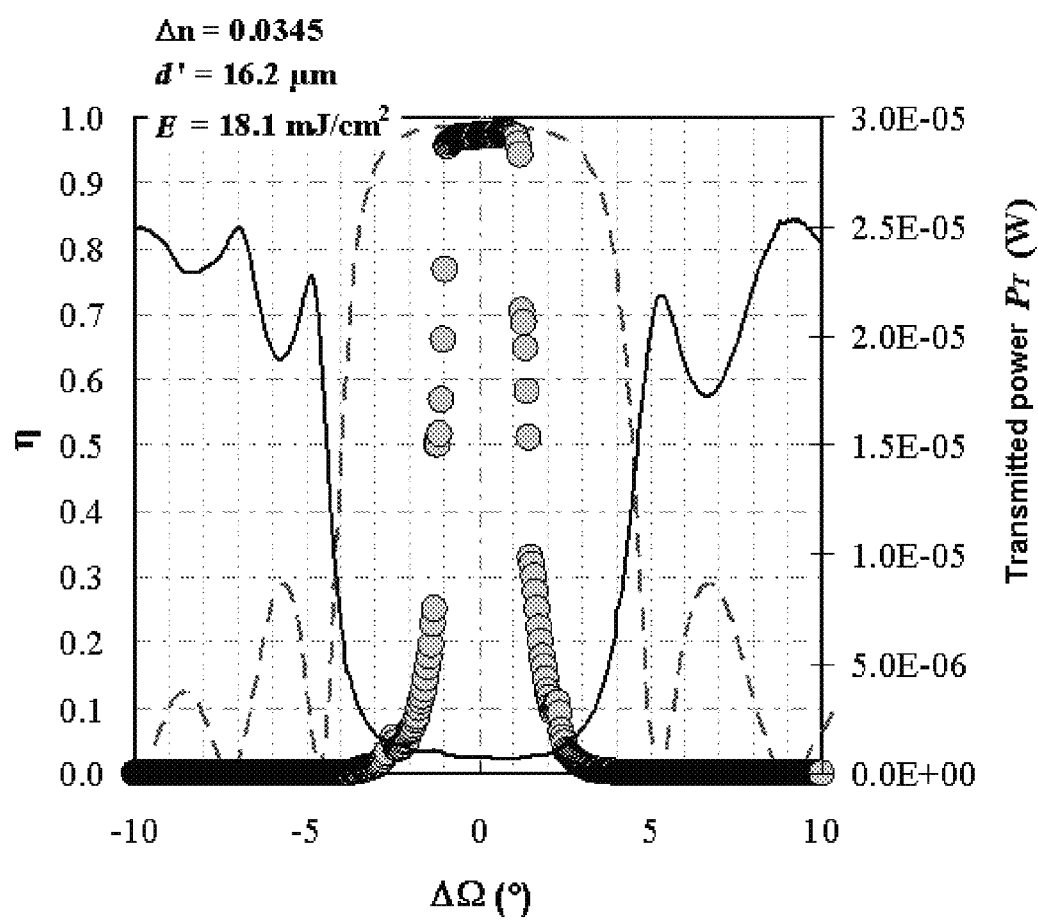
FIG. 2 illustrates a graph showing the measured transmitted power $P_T$ (right y axis) as a solid line, plotted against the angle detuning $\Delta\Omega$, the measured diffraction efficiency $\eta$ (left y axis) as solid circles, plotted against the angle detuning $\Delta\Omega$ (where permitted by the finite size of the detector) and the fit of the Kogelnik theory as a dashed line (lefty axis)

FIG. 2 shows the measured transmitted power $P_T$ (right y axis) as a solid line, plotted against the angle detuning $\Delta\Omega$ the measured diffraction efficiency $\eta$ (left y axis) as solid circles, plotted against the angle detuning $\Delta\Omega$ (where permitted by the finite size of the detector) and the fit of the Kogelnik theory as a dashed line (lefty axis).

The measured data of the diffraction efficiency, the theoretical Bragg curve and the transmitted intensity are, as shown in FIG. 2, plotted against the centred angle of rotation $\Delta\Omega = \Omega_{reconstruction} - \Omega = \alpha'_0 - \theta'_0$, also referred to as angle deturning.

Since DE is known, the shape of the theoretical Bragg curve according to Kogelnik is determined only by the thickness d' of the photopolymer layer. $\Delta n$ is subsequently corrected via DE for a given thickness d' so that measurement and theory of DE always agree. d' is now adjusted until the angle positions of the first secondary minima of the theoretical Bragg curve agree with the angle positions of the first secondary maxima of the transmitted intensity and additionally the full width at half maximum (FWHM) for the theoretical Bragg curve and for the transmitted intensity agree.

Since the direction in which a reflection hologram concomitantly rotates on reconstruction by means of an $\Omega$ scan, but the detector for the diffracted light can detect only a finite angle range, the Bragg curve of broad holograms (small d') is not completely detected in an $\Omega$ scan, but only the central region, with suitable detector positioning. The shape of the transmitted intensity which is complementary to the Bragg curve is therefore additionally used for adjusting the layer thickness d'.

FIG. 2 shows the plot of the Bragg curve $\eta$ according to the coupled wave theory (dashed line), of the measured diffraction efficiency (solid circles) and of the transmitted power (black solid line) against the angle detuning $\Delta\Omega$.

For a formulation, this procedure was possibly repeated several times for different exposure times t on different media in order to determine the average energy dose of the incident laser beam at which DE reaches the saturation value during recording of the hologram. The mean energy dose E is obtained from the powers of the two part-beams coordinated with the angles $\alpha_0$ and $\beta_0$ (reference beam with $P_r = 0.50$ mW and signal beam with $P_s = 0.63$ mW), the exposure time t and the diameter of the iris diaphragm (0.4 cm), as follows:

$$E(mJ/cm^2) = \frac{2 \cdot [P_r + P_s] \cdot t(s)}{\pi \cdot 0.4^2 \; cm^2}$$

The powers of the part-beams were adapted so that the same power density is achieved in the medium at the angles $\alpha_0$ and $\beta_0$ used.

Substances used:
CGI-909 (tetrabutylammonium tris(3-chloro-4-methylphenyl)(hexyl)borate, [1147315-11-4]) is an experimental product produced by CIBA Inc., Basle, Switzerland.

Trifluoroethanol and 1,1,1,3,3,3-hexafluoropropan-2-ol (hexafluoroisopropanol) were obtained from Sigma-Aldrich.

The urethane acrylates 1 and 2, the polyol 1 and the fluorinated urethane 1 are experimental products of Bayer MaterialScience AG, Leverkusen, Germany, and their preparation is described below.

Preparation of the urethane acrylates according to the invention:

Example 1

[(4-{[(2,2,2-trifluoroethoxy)carbonyl]
amino}phenoxy)phosphorothioyl]-bis(oxybenzene-4,
1-diylcarbamoyloxyethane-2,1-diyl)bisacrylate 0.10 g of 2,6-di-tert-butyl-4-methylphenol, 0.05 g of dibutyltin dilaurate (Desmorapid Z, Bayer MaterialScience AG, Leverkusen, Germany) and 217 g of a 27% strength solution of tris(p-isocyanatophenyl)thiophosphate in ethyl acetate (Desmodur® RFE, product of Bayer MaterialScience AG, Leverkusen, Germany) were initially introduced into a 500 ml round-bottomed flask and heated to 60° C. 12.3 g of trifluoroethanol were added and stirring was effected for a further 8 h. Thereafter, 28.9 g of 2-hydroxyethyl acrylate were added dropwise and the mixture was further kept at 60° C. until the isocyanate content had fallen below 0.1%. Thereafter, cooling was effected and ethyl acetate was completely removed in vacuo and the product was obtained as a colourless oil.

Example 2

{[4-({[(1,1,1,3,3,3-hexafluoropropan-2-yl)oxy]
carbonyl}amino)phenoxy]-phosphorothioyl}bis(oxy-
benzene-4,1-diylcarbamoyloxyethane-2,1-diyl)
bisacrylate 0.50 g of 2,6-di-tert-butyl-4-methylphenol, 0.25 g of dibutyltin dilaurate (Desmorapid Z, Bayer MaterialScience AG, Leverkusen, Germany) and and 1 kg of a 27% strength solution of tris(p-isocyanatophenyl)thiophosphate in ethyl acetate (Desmodur® RFE, product of Bayer MaterialScience AG, Leverkusen, Germany) were initially introduced into a 2 l round-bottomed flask and heated to 60° C. 95.3 g of hexafluoroisopropanol were added and stirring was effeted for a further 8 h. Thereafter, 135.5 g of 2-hydroxyethyl acrylate were added dropwise and the mixture was further kept at 60° C. until the isocyanate content had fallen below 0.1%. Thereafter, cooling was effected and the ethyl acetate was completely removed in vacuo and the product was obtained as a colourless oil.

Example 3

2-{[(4-{[bis(4-{[(2,2,2-trifluoroethoxy)carbonyl]amino}phenoxy)phosphorothioyl]oxy}phenyl)carbamoyl]oxy}ethyl acrylate 0.10 g of 2,6-di-tert-butyl-4-methylphenol, 0.05 g of dibutyltin dilaurate (Desmorapid Z, Bayer MaterialScience AG, Leverkusen, Germany) and and 222 g of a 27% strength solution of tris(p-isocyanatophenyl)thiophosphate in ethyl acetate (Desmodur® RFE, product of Bayer MaterialScience AG, Leverkusen, Germany) were initially introduced into a 500 ml round-bottomed flask and heated to 60° C. 25.5 g of trifluoroethanol were added and stirring was further effected until the NCO content was 1.9% by weight of NCO. Thereafter, 14.6 g of 2-hydroxyethyl acrylate were added dropwise and the mixture was further kept at 60° C. until the isocyanate content had fallen below 0.1%. Thereafter, cooling was effected and the ethyl acetate was completely removed in vacuo and the product was obtained as a colourless oil.

Example 4

[(4-{[(2,2,2-trifluoroethoxy)carbonyl]amino}phenoxy)phosphorothioyl]-bis(oxybenzene-4,1-diylcarbamoyloxybutane-4,1-diyl)bisacrylate 0.10 g of 2,6-di-tert-butyl-4-methylphenol, 0.05 g of dibutyltin dilaurate (Desmorapid Z, Bayer MaterialScience AG, Leverkusen, Germany) and and 201 g of a 27% strength solution of tris(p-isocyanatophenyl)thiophosphate in ethyl acetate (Desmodur® RFE, product of Bayer MaterialScience AG, Leverkusen, Germany) were initially introduced into a 500 ml round-bottomed flask and heated to 60° C. 11.5 g of trifluoroethanol were added and stirring was further effected until the NCO content was 1.9% by weight of NCO. Thereafter, 33.6 g of 2-hydroxybutyl acrylat were added dropwise and the mixture was further kept at 60° C. until the isocyanate content had fallen below 0.1%. Thereafter, cooling was effected and the ethyl acetate was completely removed in vacuo and the product was obtained as a colourless oil.

Example 5

{[4-({[(1,1,1,3,3,3-hexafluoropropan-2-yl)oxy]carbonyl}amino)phenoxy]-phosphorothioyl}bis(oxybenzene-4,1-diylcarbamoyloxybutane-4,1-diyl)bisacrylate 0.02 g of 2,6-di-tert-butyl-4-methylphenol, 0.01 g of dibutyltin dilaurate (Desmorapid Z, Bayer MaterialScience AG, Leverkusen, Germany) and and 47.0 g of a 27% strength solution of tris(p-isocyanatophenyl)thiophosphate in ethyl acetate (Desmodur® RFE, product of Bayer MaterialScience AG, Leverkusen, Germany) were initially introduced into a 250 ml round-bottomed flask and heated to 60° C. 4.5 g of hexafluoroisopropanol were added and stirring was effected for a further 8 h. Thereafter, 7.8 g of 2-hydroxybutyl acrylate were added dropwise and the mixture was further kept at 60° C. until the isocyanate content had fallen below 0.1%. Thereafter, cooling was effected and ethyl acetate was completely removed in vacuo and the product was obtained as a colourless oil.

Preparation of the Comparative urethane-acrylates

Preparation of urethane acrylate 1: phosphorothioyl-tris(oxybenzene-4,1-diylcarbamoyl-oxyethane-2,1-diyl)trisacrylate 0.1 g of 2,6-di-tert-butyl-4-methylphenol, 0.05 g of dibutyltin dilaurate (Desmorapid Z, Bayer MaterialScience AG, Leverkusen, Germany) and and 213.0 g of a 27% strength solution of tris(p-isocyanatophenyl)thiophosphate in ethyl acetate (Desmodur® RFE, product of Bayer MaterialScience AG, Leverkusen, Germany) were initially introduced into a 500 ml round-bottomed flask and heated to 60° C. Thereafter, 42.37 g of 2-hydroxyethyl acrylate were added dropwise and the mixture was further kept at 60° C. until the isocyanate content had fallen below 0.1%. Thereafter, cooling was effected and the ethyl acetate was completely removed in vacuo. The product was obtained as a semicrystalline solid.

Preparation of urethane acrylate 2: 2-({[3-(methylsulphanyl)phenyl]carbamoyl}oxy)-propylethyl prop-2-enoate 0.05 g of 2,6-di-tert-butyl-4-methylphenol, 0.02 g of Desmorapid Z, 26.8 g 3-(methylthio)phenyl isocyanate in 50 g of ethyl acetate were initially introduced into a 250 ml round-bottomed flask and heated to 60° C. Thereafter, 21.1 g of 2-hydroxyethyl acrylate were added dropwise and the mixture was further kept at 60° C. until the isocyanate content had fallen below 0.1%. Thereafter, the ethyl acetate was distilled off at 5 mbar and cooling was effected. The product was obtained as a light yellow liquid.

Preparation of the fluorinated urethane 1: 2,2,3,3,4,4,5,5,6,6,7,7,8,8,9,9-hexadecafluorononyl-butyl carbamate 0.50 g of Desmorapid Z and 186 g of n-butyl isocyanate were initially introduced into a 1 l round-bottomed flask and heated to 60° C. Thereafter, 813 g of 2,2,3,3,4,4,5,5,6,6,7,7,8,8,9,9-hexadecafluorononanol were added dropwise and the mixture was further kept at 60° C. until the isocyanate content had fallen below 0.1%. Cooling was then effected. The product was obtained as a colourless oil.

Preparation of the Polyol Component:

Polyol 1:

0.18 g of tin octanoate, 374.8 g of ε-caprolactone and 374.8 g of a difunctional polytetrahydrofuranpolyetherpolyol (equivalent weight 500 g/mol OH) were initially introduced into a 1 l flask and heated to 120° C. and kept at this temperature until the solids content (proportion of nonvolatile constituents) was 99.5% by weight or more. Thereafter, cooling was effected and the product was obtained as a waxy solid.

Summary of the measured refractive indices of the compounds used here:

TABLE 1

Refractive indices of the compounds used
in the examples and comparative examples

| Compound | Refractive index (405 nm) |
|---|---|
| Example 1 | 1.626 |
| Example 2 | 1.616 |
| Example 3 | 1.606 |
| Example 4 | 1.616 |
| Example 5 | 1.611 |
| Urethane acrylate 1 | 1.624 |
| Urethane acrylate 2 | 1.626 |
| | Refractive index $n_D^{20}$ |
| Fluorourethane 1 | 1.3555 |

Production of the Media

Medium 1:

3.40 g of the polyol component prepared as described above were mixed with 3.50 g of {[4-({[(1,1,1,3,3,3-hexafluoropropan-2-yl)oxy]carbonyl}amino)phenoxy] phosphorothioyl}bis(oxy-benzene-4,1-diylcarbamoyloxy-ethane-2,1-diyl)bisacrylate (Example 2), 0.50 g of 2-({[3-(methyl-sulphanyl)phenyl]carbamoyl}oxy)ethyl prop-2-enoate(urethane acrylate 2), 1.50 g of 2,2,3,3,4,4,5,5,6,6,7,7,8,8,9,9-hexadecafluorononyl butylcarbamate (fluorinated urethane 1), 0.10 g of CGI 909 (experimental product of Ciba Inc, Basle, Switzerland), 0.01 g of new methylene blue and 0.35 g of N-ethylpyrrolidone at 60° C. so that a clear solution was obtained. Thereafter, cooling to 30° C. was effected, 0.63 g of Desmodur N3900 (commercial product of Bayer MaterialScience AG, Leverkusen, Germany, hexane diisocyanate-based polyisocyanate, proportion of imino-oxadiazinedione at least 30%, NCO content: 23.5%) was added and mixing was effected again. Finally, 0.006 g of Fomrez UL 28 (urethanization catalyst, commercial product of Momentive Performance Chemicals, Wilton, Conn., USA) was added and mixing was effected again briefly. The liquid material obtained was then poured onto a glass plate and covered there with a second glass plate which was kept at a distance of 20 µm by spacers. This test specimen was left standing for 12 hours at room temperature and cured.

In example media 2-6, the polyol component and Desmodur N3900 (commercial product of Bayer MaterialScience AG, Leverkusen, Germany, hexane diisocyanate-based polyisocyanate, proportion of iminooxadiazinedione at least 30%, NCO content: 23.5%) were always used as matrix building blocks, in particular so that the NCO:OH ratio was 1.02:1 and the total percentage by weight is 100%. All experiments were carried out with 15% of 2,2,3,3,4,4,5,5,6,6,7,7,8,8,9,9-hexadecafluorononyl butylcarbamate (fluorinated urethane 1), 0.1% of new methylene blue and 1.0% of CGI 909 (experimental product of Ciba Inc, Basle, Switzerland), dissolved in 3.5% of N-ethylpyrrolidone, and the stated amount of a 10% strength solution of catalyst 1 in N-ethyl-pyrrolidone. The contents of Example 2 and urethane acrylate 2 were varied as described in Table 2. In each case the maximum value in Δn is reported, and doses used are between 4 and 64 mJ/cm$^2$ per arm.

Comparative Medium I:

3.40 g of the polyol component prepared as described above were mixed with 4.00 g of phosphorothioyltris(oxy-benzene-4,1-diylcarbamoyloxyethane-2,1-diyl)trisacrylate (urethane acrylate 1), 1.50 g of 2,2,3,3,4,4,5,5,6,6,7,7,8,8,9,9-hexadecafluorononyl butylcarbamate (fluorinated urethane 1), 0.10 g of CGI 909 (experimental product of Ciba Inc, Basle, Switzerland), 0.01 g of new methylene blue and 0.35 g of N-ethylpyrrolidone at 60° C. so that a clear solution was obtained. Thereafter, cooling to 30° C. was effected, 0.64 g of Desmodur N3900 (commercial product of Bayer Material-Science AG, Leverkusen, Germany, hexane diisocyanate-based polyisocyanate, proportion of iminooxadiazinedione at least 30%, NCO content: 23.5%) was added and mixing was effected again. Finally, 0.006 g of Fomrez UL 28 (urethanization catalyst, commercial product of Momentive Performance Chemicals, Wilton, Conn., USA) was added and mixing was effected again briefly. The liquid material obtained was then poured onto a glass plate and covered there with a second glass plate which was kept at a distance of 20 µm by spacers. This test specimen was left standing for 12 hours at room temperature and cured.

In comparative media II-VIII, the polyol component and Desmodur N3900 (commercial product of Bayer Material-Science AG, Leverkusen, Germany, hexane diisocyanate-based polyisocyanate, proportion of iminooxadiazeinedione at least 30%, NCO content: 23.5%) were always used as matrix building blocks, in particular so that the NCO:OH ratio was 1.02:1 and the total percentage by weight is 100%. All experiments were carried out with 15% of 2,2,3,3,4,4,5,5,6,6,7,7,8,8,9,9-hexadecafluorononyl butylcarbamate (fluorinated urethane 1), 0.1% of new methylene blue and 1.0% of CGI 909 (experimental product of Ciba Inc, Basle, Switzerland), dissolved in 3.5% of N-ethylpyrrolidone, and the stated amount of a 10% strength solution of catalyst 1 in N-ethyl-pyrrolidone. The contents of urethane acrylate 1 and urethane acrylate 2 were varied as described in Table 2. In each case the maximum value in Δn is reported, and doses used are between 4 and 64 mJ/cm$^2$ per arm.

TABLE 2

Example media for variation of the double bond density by variation of the content of Example 2 relative to urethane acrylate 2

| Medium | Example 2 (% by wt.) | Urethane acrylate 2 (% by wt.) | Double bond density (eq/kg) | Δn | Peak shift |
|---|---|---|---|---|---|
| 1 | 35.0 | 5.0 | 0.986 | 0.0210 | 2.900 |
| 2 | 30.0 | 10.0 | 1.048 | 0.0260 | 3.000 |
| 3 | 20.0 | 20.0 | 1.172 | 0.0300 | 3.500 |
| 4 | 15.0 | 25.0 | 1.234 | 0.0303 | 3.900 |
| 5 | 10.0 | 30.0 | 1.296 | 0.0310 | 4.100 |
| 6 | 5.0 | 35.0 | 1.358 | 0.0323 | 4.400 |

TABLE 3

Comparative examples for variation of the double bond density by variation of the content of urethane acrylate 1 relative to urethane acrylate 2

| Comparative medium | Urethane acrylate 1 (% by wt.) | Urethane acrylate 2 (% by wt.) | Double bond density (eq/kg) | Δn | Peak shift |
|---|---|---|---|---|---|
| I | 40.0 | 0.0 | 1.476 | 0.0200 | 3.000 |
| II | 30.0 | 10.0 | 1.462 | 0.0310 | 3.620 |
| III | 25.0 | 15.0 | 1.455 | 0.0314 | 3.900 |
| IV | 20.0 | 20.0 | 1.448 | 0.0337 | 4.450 |
| V | 15.0 | 25.0 | 1.441 | 0.0342 | 4.500 |
| VI | 10.0 | 30.0 | 1.434 | 0.0354 | 4.450 |
| VII | 5.0 | 35.0 | 1.427 | 0.0367 | 4.700 |
| VIII | 0.0 | 40.0 | 1.420 | 0.0400 | 4.900 |

Figure 3:
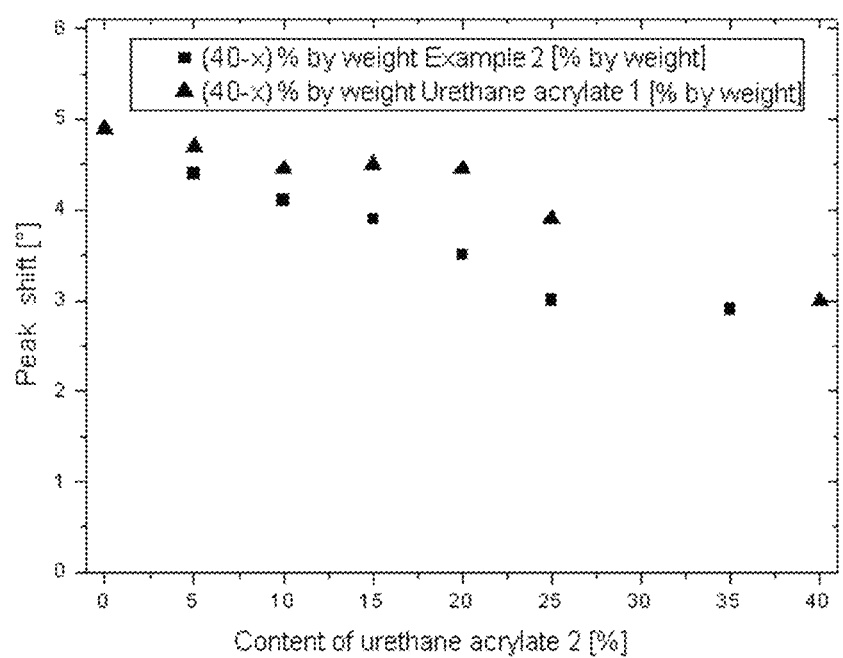
FIG. 3 illustrates a graph showing the dependence of the peak shift on the total composition as reproduced in Table 2 (Examples 1-6) and Table 3 (Examples I-VIII).

FIG. 3 shows the dependence of the peak shift on the total composition as reproduced in Table 2 (Examples 1-6) and Table 3 (Examples I-VIII). By using Example 2, the peak shift in the optical grating can be substantially reduced compared with the use of urethane acrylate 1. This is particularly clear if in each case 20% by weight of Example 2 or 20% by weight of urethane acrylate 1 with in each case 20% by weight of the monofunctional urethane acrylate 2 are used, as in medium 3 and in comparative medium IV. In the case of similarly bright holograms (Δn (medium 3)=0.0300 vs. Δn (comparative medium IV)=0.0330), a substantially reduced peak shift of 3.500° is observed in medium 3 compared with 4.450° in comparative medium IV. This shows that, when used in photopolymer formulations, the urethane acrylates according to the invention permit the recording of holograms having increased trueness of angle and trueness of colour.

The invention claimed is:

1. A photopolymer formulation comprising matrix polymers, writing monomers and photoinitiators, wherein the writing monomers comprise a urethane acrylate of the formula (I)

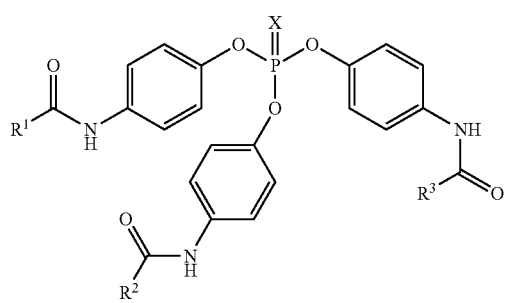

wherein

X represents oxygen or sulphur, and $R^1$, $R^2$, $R^3$, independently of one another, represent an olefinically unsaturated organic radical or an aliphatic alcohol, wherein at least one of the radicals $R^1$, $R^2$, $R^3$ represents an olefinically unsaturated organic radical and at least one of the radicals $R^1$, $R^2$, $R^3$ represents an aliphatic alcohol and wherein the photopolymer formulation further comprises urethanes as plasticizers, wherein the urethanes are substituted by at least one fluorine atom.

2. The photopolymer formulation according to claim 1, wherein the matrix polymers comprise polyurethanes.

3. The photopolymer formulation according to claim 1, wherein the photoinitiators comprise an anionic, cationic or neutral dye and a coinitiator.

4. The photopolymer formulation according to claim 1, wherein the urethanes have the formula (III)

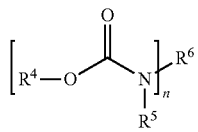

wherein n is from 1 to 8 and $R^4$, $R^5$, $R^6$ independently of one another, represent hydrogen or linear, branched, cyclic or heterocyclic organic radicals which are unsubstituted or optionally substituted by heteroatoms.

5. The photopolymer formulation according to claim 4, wherein at least one of the radicals $R^4$, $R^5$, $R^6$ are substituted by at least one fluorine atom.

6. The photopolymer formulation according to claim 4, wherein $R^4$ represents an organic radical having at least one fluorine atom.

7. The photopolymer formulation according to claim 1, wherein the writing monomers further comprise a monofunctional writing monomer.

8. The photopolymer formulation according to claim 1, wherein the writing monomers further comprise a monofunctional acrylate.

9. The photopolymer formulation according to claim 8, wherein the monofunctional acrylate has the formula (IV)

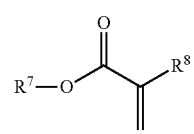

wherein $R^7$, $R^8$ independently of one another, represent hydrogen or linear, branched, cyclic or heterocyclic organic radicals which are unsubstituted or optionally also substituted by heteroatoms.

10. The photopolymer formulation according to claim 1, wherein the writing monomers further comprise a monofunctional urethane acrylate.

11. The photopolymer formulation according to claim 1, wherein the aliphatic alcohol or alcohols is or are substituted by at least one fluorine atom.

12. The photopolymer formulation according to claim 1, wherein the aliphatic alcohol or alcohols has or have linear or branched C1-C10 radicals.

13. The photopolymer formulation according to claim 1, wherein the aliphatic alcohol or alcohols has or have linear $C_2$-$C_4$ or branched $C_3$-alkyl radicals.

14. The photopolymer formulation according to claim 1, wherein the aliphatic alcohols comprise trifluoroethanol and/or 1,1,1,3,3,3-hexafluoropropan-2-ol.

15. The photopolymer formulation according to claim 1, wherein the olefinically unsaturated organic radical or radicals comprise acrylate or methacrylate structures.

16. The photopolymer formulation according to claim 1, wherein the olefinically unsaturated organic radical or radicals is or are substituted by one or more heteroatoms.

17. A method comprising forming in-line holograms, off-axis holograms, full aperture transfer holograms, white light transmission holograms, Denisyuk holograms, off-axis reflection holograms, edge-lit holograms or holographic stereograms, wherein the holograms or stereograms are produced with the photopolymer formulation according to claim 1 by exposure to recording light.

* * * * *